(12) United States Patent
Sosic et al.

(10) Patent No.: US 8,232,064 B2
(45) Date of Patent: Jul. 31, 2012

(54) DETECTION AND QUANTITATION OF CYCLODEXTRINS

(75) Inventors: Zoran Sosic, Cambridge, MA (US); Rulin Qian, Canton, MA (US); James Ahern, Winchester, MA (US); Rohin Mhatre, Lexington, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 873 days.

(21) Appl. No.: 11/720,920

(22) PCT Filed: Dec. 5, 2005

(86) PCT No.: PCT/US2005/043869
§ 371 (c)(1),
(2), (4) Date: Dec. 8, 2008

(87) PCT Pub. No.: WO2006/062881
PCT Pub. Date: Jun. 15, 2006

(65) Prior Publication Data
US 2009/0227039 A1    Sep. 10, 2009

Related U.S. Application Data

(60) Provisional application No. 60/633,162, filed on Dec. 6, 2004.

(51) Int. Cl.
*G01N 31/00* (2006.01)
*G01N 33/53* (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search .................. None
See application file for complete search history.

(56) References Cited

U.S. PATENT DOCUMENTS
2004/0106199 A1    6/2004    Eliseev

OTHER PUBLICATIONS

Gage et al. Journal of Pharmaceutical and Biomedical Analysis. vol. 22, pp. 773-780, 2000.*
Bayliss, M.A.J., et al., "Fluorescence Determination of Sulphobutylether-β-Cyclodextrin Sodium in Human Plasma and Urine by Size-Exclusion Chromatography with Inclusion Complex Formation," *Chromatographia 52 (Suppl)*:S83-S86, Friedr. Vieweg & Sohn Verlagsgesellschaft mbH (2000).
Christian, A.E., et al., "Comparison of the capacity of β-cyclodextrin derivatives and cyclophanes to shuttle cholesterol between cells and serum lipoproteins," *J. Lipid Res. 40*:1475-1482, Federation of American Societies for Experimental Biology (1999).
Gage, R., et al., "Fluorescence determination of sulphobutylether-β-cyclodextrin in human plasma by size exclusion chromatography with inclusion complex formation," *J. Pharm. Biomed. Anal. 22*:773-780, Elsevier Science B.V. (2000).
Grosse, P.Y., et al., "High-performance liquid chromatographic assay for methyl-β-cyclodextrin in plasma and cell lysate," *J. Chromatogr. B 694*:219-226, Elsevier Science B.V. (1997).
Massey, K.A., et al. "Determination of carbaryl as its primary metabolite, 1-naphthol, by reversed-phase high-performance liquid chromatography with fluorometric detection" *Talanta 42*:1457-1463, Elsevier Science Ltd. (1995).
Fukuda et al., "Microanalyses of beta-cyclodextrin and glucosyl-beta-cyclodextrin in biological matrices by high performance liquid chromatography with pulsed amperometric detection." *Anal. Biochem. 212*(1):289-91 (1993).
Haginaka J. et al., "Detection of cyclodextrins in serum by reversed-phase chromatography with pulsed amperometric detection and membrane reactor," *J. Pharm. Biomed. Anal. 11*(10):1023-6 (1993).
Zhang et al., "Study on inclusion compounds of β-cyclodextrin with α- and β-naphthol," *Journal of Northwest Normal University (Natural Science) 36*(1): 70-74 (2000).

* cited by examiner

*Primary Examiner* — Lisa Cook
(74) *Attorney, Agent, or Firm* — Sterne, Kessler, Goldstein & Fox, P.L.L.C.

(57) ABSTRACT

The invention relates to the detection and quantitation of cyclodextrins and cyclodextrin derivatives in solutions comprising a protein. The invention further relates to methods of evaluating pharmaceutical preparations for the presence of residual cyclodextrins.

60 Claims, 3 Drawing Sheets

DETECTION AND QUANTITATION OF CYCLODEXTRINS

BACKGROUND OF THE INVENTION

1. Field of the Invention

The invention relates to the detection and quantitation of cyclodextrins and cyclodextrin derivatives in solutions comprising a protein. The invention further relates to methods of evaluating pharmaceutical preparations for the presence of residual cyclodextrins.

2. Background

Cyclodextrins are cyclic polysaccharides most commonly consisting of six (α-cyclodextrin), seven (β-cyclodextrin), or eight (γ-cyclodextrin) glucose units linked by alpha-1,4-glucosidic bonds in a donut shaped ring. As a consequence of the chair formation of the sugar units, all secondary hydroxyl units are located on one side of the ring, while all of the primary hydroxyl groups are situated on the other side. As a result, the external faces are hydrophilic, making the cyclodextrins water-soluble. In contrast, the cavities of the cyclodextrins are hydrophobic, since they are lined by the hydrogens of atoms $C_3$ and $C_5$ and by ether-like oxygens. This structure allows cyclodextrins to form inclusion complexes with hydrophobic compounds. Based on this characteristic, cyclodextrins are widely used to increase the solubility of poorly water soluble pharmaceuticals, enhance pharmaceutical stability, and reduce unwanted side effects of pharmaceuticals.

The hydroxyl groups of cyclodextrins may be derivatized to alter the characteristics of the molecule (e.g., water solubility, binding specificity). Methyl-β-cyclodextrin (MBCD) is one of the most frequently used cyclodextrin derivatives.

Cyclodextrins are also used in cell culture systems to carry hydrophobic nutrients, such as cholesterol, into cells. Cyclodextrins are particularly useful for the culturing of cholesterol auxotrophic cells, e.g., cholesterol auxotrophic CHO cells, COS cells, and NSO cells. When cell cultures are used to produce naturally occurring or recombinant proteins, particularly therapeutic proteins, the presence of cyclodextrins as a residual contaminant in the purified protein product is an issue in the production of pharmaceutical products. Thus, a sensitive and rapid technique for the detection and quantification of low levels of cyclodextrins or cyclodextrin derivatives in a solution comprising a protein is needed.

Grosse et al. (*J. Chromatography B* 694:219 (1997)) disclose a technique for detecting MBCD using size exclusion chromatography in the presence of a fluorophore (1-naphthol) that forms an inclusion complex with MBCD and allows fluorescent detection of the inclusion complex. This technique, which was designed for the detection of MBCD in plasma samples for pharmacokinetic studies, requires extraction of samples with organic solvents, evaporation, and dissolution of the residue in the mobile phase prior to chromatography. Gage et al. (*J. Pharm. Biomed. Analysis* 22:773 (2000)) disclose a similar technique using 1-naphthol for measuring the presence of sulphobutylether-β-cyclodextrin in plasma samples. This method requires processing of the sample, including solid phase extraction, evaporation, and dissolution of the residue, prior to chromatography. These techniques do not achieve separation of cyclodextrins from protein components.

A need exists in the art for a method of testing for the presence of cyclodextrins or cyclodextrin derivatives in the presence of a protein, preferably without the need for sample extraction steps.

SUMMARY OF THE INVENTION

Accordingly, in one aspect, the invention provides a method for testing for the presence of a cyclodextrin or cyclodextrin derivative in a solution comprising a protein, the method comprising separating any cyclodextrin or cyclodextrin derivative that may be present from said protein by size exclusion chromatography (SEC), contacting said cyclodexirin or cyclodextrin derivative with an agent that forms a detectable inclusion complex with a separated cyclodextrin or cyclodextrin derivative, and measuring for the presence of a signal from said inclusion complex.

Another aspect of the invention is a method for determining the quantity of a cyclodextrin or cyclodextrin derivative that may be present in a solution comprising a protein, the method comprising separating any cyclodextrin or cyclodextrin derivative from said protein by SEC, contacting said cyclodextrin or cyclodextrin derivative with an agent that forms a detectable inclusion complex with a separated cyclodextrin or cyclodextrin derivative, measuring for the presence of a signal from said inclusion complex, and determining the size of said signal, wherein the size of the signal is indicative of the quantity of the cyclodextrin or cyclodextrin derivative in the solution.

A third aspect of the invention is a method of evaluating a pharmaceutical preparation, the method comprising:

(a) providing a pharmaceutical preparation comprising a therapeutic protein and a pharmaceutically acceptable carrier;

(b) separating said pharmaceutical preparation by SEC;

(c) contacting any cyclodextrin or cyclodextrin derivative that may be present in the pharmaceutical preparation with an agent that forms a detectable inclusion complex with a separated cyclodextrin or cyclodextrin derivative; and (d) detecting a signal from said inclusion complex, wherein the size of the signal is indicative of the quantity of the cyclodextrin or cyclodextrin derivative in the preparation.

In one embodiment of the invention the cyclodextrin or cyclodextrin derivative is MBCD.

In another embodiment of the invention the agent is a fluorophore, e.g., 1-naphthol. The agent may be brought in contact with the cyclodextrin or cyclodextrin derivative prior to, during, or after the separation by SEC.

In one embodiment a sample of the solution or the pharmaceutical preparation is loaded on the SEC column without any preparation, e.g., the sample is not extracted with organic solvents, dried, resuspended, concentrated, or otherwise altered.

DETAILED DESCRIPTION OF THE INVENTION

Figure 1:
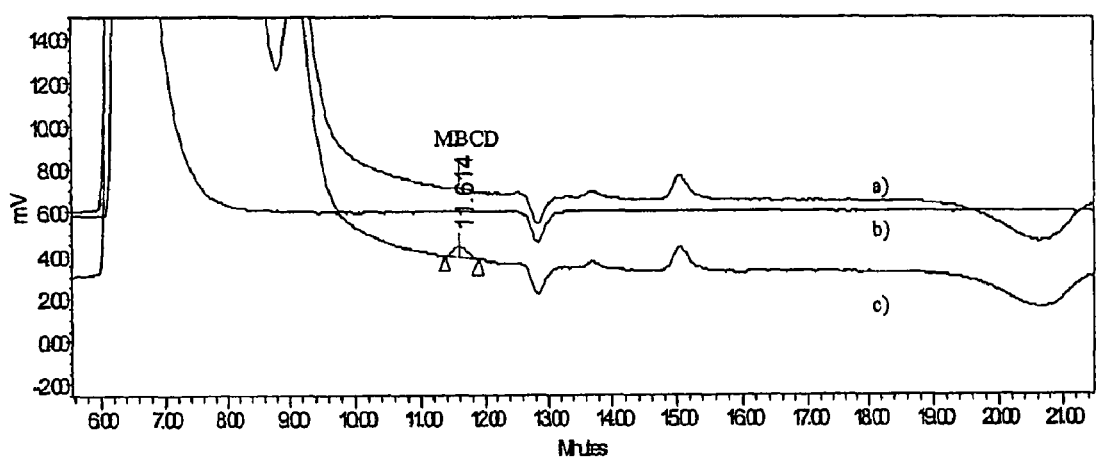
FIG. 1 shows representative chromatograms for a pharmaceutical preparation of purified natilizumab with and without MBCD. (a) pharmaceutical preparation (19.6 mg/mL natilizumab); (b) formulation buffer; (c) pharmaceutical preparation (19.6 mg/mL natilizumab) spiked with 1.3 μg/mL MBCD.

The present invention relates to the detection and quantitation of low levels of a cyclodextrin or a cyclodextrin derivative in a solution comprising a protein. In one embodiment, the methods of the invention are useful for the evaluation of purified proteins prepared from cells grown in the presence of a cyclodextrin or a cyclodextrin derivative for the presence of residual cyclodextrin. Accordingly, in one aspect, the invention provides a method for testing for the presence of a cyclodextrin or cyclodextrin derivative in a solution comprising a protein, the method comprising separating any cyclodextrin or cyclodextrin derivative that may be present from said protein by size exclusion chromatography (SEC), contacting said cyclodextrin or cyclodextrin derivative with an agent that forms a detectable inclusion complex with a separated cyclodextrin or cyclodextrin derivative, and measuring for the presence of a signal from said inclusion complex.

Another aspect of the invention is a method for determining the quantity of a cyclodextrin or cyclodextrin derivative that may be present in a solution comprising a protein, the method comprising separating any cyclodextrin or cyclodextrin derivative from said protein by SEC, contacting said cyclodextrin or cyclodextrin derivative with an agent that forms a detectable inclusion complex with a separated cyclodextrin or cyclodextrin derivative, measuring for the presence of a signal from said inclusion complex, and determining the size of said signal, wherein the size of the signal is indicative of the quantity of the cyclodextrin or cyclodextrin derivative in the solution.

A third aspect of the invention is a method of evaluating a pharmaceutical preparation, the method comprising:
(a) providing a pharmaceutical preparation comprising a therapeutic protein and a pharmaceutically acceptable carrier;
(b) separating said pharmaceutical preparation by SEC;
(c) contacting any cyclodextrin or cyclodextrin derivative that may be present in the pharmaceutical preparation with an agent that forms a detectable inclusion complex with a separated cyclodextrin or cyclodextrin derivative; and
(d) detecting a signal from said inclusion complex, wherein the size of the signal is indicative of the quantity of the cyclodextrin or cyclodextrin derivative in the preparation.

The term "cyclodextrin or cyclodextrin derivative," as used herein, refers to any known cyclodextrin, particularly α-cyclodextrin, β-cyclodextrin, and γ-cyclodextrin, and any known cyclodextrin derivative. Cyclodextrin derivatives are disclosed in U.S. Pat. Nos. 3,426,011, 3,453,257, 3,453,258, 3,453,259, 3,453,260, 3,459,731, 3,553,191, 3,565,887, 4,383,992, 4,535,152, 4,616,008, 4,638,058, 4,659,696, 4,746,734, 4,678,598, 5,594,125, 5,710,268, and 5,831,081, each of which is incorporated by reference. Examples of cyclodextrin derivatives include MBCD, hydroxyethyl-β-cyclodextrin, and hydroxypropyl-β-cyclodextrin. Cyclodextrins and cyclodextrin derivatives are available from American Maize Products Company, Wacker Chemicals (USA), Inc., and Sigma-Aldrich Chemical Company.

The term "agent that can form a detectable inclusion complex with a cyclodextrin or a cyclodextrin derivative," as used herein, refers to any agent that is capable of forming an inclusion complex with a cyclodextrin or a cyclodextrin derivative, wherein the inclusion complex is capable of detection upon elution from a SEC column. The term includes agents that are not inherently detectable but contain a detectable label, e.g., a radionuclide or a fluorescent tag. The term also includes agents that are not inherently detectable but form a detectable inclusion complex with a cyclodextrin or cyclodextrin derivative. Examples of methods of detection include, but are not limited to, fluorescent detection, ultraviolet detection, radiometric detection, colorimetric detection, fluorescence polarization, evaporative light-scattering, capillary electrophoresis, infrared spectroscopy, $^1$H NMR, and mass spectroscopy. In one embodiment the detectable agent is a fluorophore, e.g., 1-naphthol. Other detectable agents, such as phenolphthalein and 8-anilinonaphthalene-1-sulfonic acid, may be used as well.

The term "therapeutic protein," as used herein, refers to any peptide or protein that is known to be useful for the prevention, treatment, or amelioration of a disease or disorder, e.g., an antibody, growth factor, cell surface receptor, cytokine, hormone, toxin, or fragments and/or fusion proteins of any of the foregoing. The term "antibody" is used in its broadest sense to include monoclonal antibodies, chimeric, humanized, or fully human antibodies, and antigen-binding antibody fragments and/or derivatives thereof, such as single chain antibodies, light chain and heavy chain dimers, and Fv, Fab, and (Fab')$_2$ fragments. Examples of therapeutic proteins include, but are not limited to, proteins such as erythropoietin, growth hormone, colony stimulating factor, insulin, and therapeutic antibodies such as natilizumab, infliximab, adalimumab, MabThera, Herceptin, Palivizumab, Abciximab, Alemtuzumab, OKT3-muromonab-CD3, Basiliximab, Gemtuzumab ozogamicin, Omalizumab, Ibritumomab tiuxetan, Edrecolomab-Mab17-1A, Tositumomab, efalizumab, bevacizumab, and cetuximab. The protein may be isolated from cells in which it is naturally occurring or cells that have been genetically engineered to express it, e.g., recombinantly expressed.

The terms "at least 90% (or higher) pure" and "at least 90% (or higher) homogeneity," as used herein, refer to a protein that has been purified away from other proteins, lipids, nucleic acids and other cellular components such that the protein makes up at least 90% (or higher) by dry weight of the purified preparation. In some embodiments, a protein may be at least 91%, 92%, 93%, 94%, 95%, 96%, 97%, 98%, or 99% pure.

The term "derivative thereof," as used to refer to a cell line described herein, refers to any cells created from that cell line that have at least one new characteristic. Examples of cell derivatives having a new characteristic include, but are not limited to, cells having a different growth pattern (e.g., cholesterol auxotrophy) such as can be generated by selective pressure, and cells that are genetically engineered to express a protein or exhibit some other new behavior.

In the methods of the present invention, the SEC column may be any suitable size and contain any SEC medium suitable for the separation of a cyclodextrin or a cyclodextrin derivative from a protein. In one embodiment, the SEC medium has a separation range from about 5-20 kDa to about 75-300 kDa The SEC medium may have a particle size of about 2 to about 6 microns, preferably about 3-5 microns, e.g., about 4 microns. One example of a suitable SEC medium is TSK gel G2000 SW$_{XL}$ (Tosoh Biosciences, Inc.). Another suitable SEC medium is a polymer-based TSK gel column. In a preferred embodiment, the separation is performed by high pressure liquid chromatography (HPLC). For HPLC, a suitable size for the SEC column is in the range of about 5 to about 15 mm in diameter and about 3 to about 60 cm in length. Sample sizes may be in the range of about 10 to about 500 μL, preferably about 50 to about 100 μL.

The sample to be loaded on the SEC column can be a sample from any solution comprising a protein and for which it is desired to test for the presence of a cyclodextrin or a cyclodextrin derivative. In one embodiment of the invention, the sample is from a solution that contains a protein that is in the process of being purified or has been purified and in which it is desirable to determine the presence or quantity of a cyclodextrin or a cyclodextrin derivative. In one embodiment the protein has been purified or is being purified from cells grown in cell culture in the presence of a cyclodextrin or a cyclodextrin derivative. The sample may be from a solution at any stage of the purification process for the protein, e.g., after cell lysis, after one or more purification steps (such as ion exchange chromatography, affinity chromatography, etc.), or after the final purification step. The protein in the solution may be at least 90% pure, preferably at least 95%, 96%, 97%, 98%, or 99% pure. In one embodiment, the sample is from a solution that has less than 20 µg/mL, preferably less than 10 µg/mL, 5 µg/mL, 2 µg/mL, or 1 µg/mL of the cyclodextrin or cyclodextrin derivative.

The sample may be taken from the solution comprising the protein and loaded directly on the SEC column as long as the buffer of the solution is suitable for SEC. If necessary, the buffer of the sample may be adjusted to be suitable for SEC. A suitable buffer for SEC is an aqueous buffer having a pH between about 2.0 and about 8.0, preferably between about 5.0 and about 7.5. Examples of suitable buffers include, but are not limited to, sodium phosphate, potassium phosphate, sodium acetate, sodium citrate, potassium nitrate, and Tris-HCl. The buffer should also comprise sufficient salt to prevent the protein in the sample from sticking to the column and the SEC medium. Suitable levels of salt are in the range of about 50 mM to about 300 mM, preferably about 100 mM to about 200 mM, more preferably about 140 mM. Examples of salts that may be used include, but are not limited to, sodium chloride, potassium chloride, sodium sulfate, potassium sulfate, magnesium sulfate, ammonium sulfate, ammonium phosphate, and magnesium chloride. Preferably the salt is sodium chloride.

In one embodiment of the invention, the sample does not undergo any preparation steps other than adjustment of the buffer as necessary. For example, the sample is not extracted (e.g., with an organic solvent or with a solid phase cartridge), dried, resuspended, concentrated, or otherwise altered. The ability to load samples directly on the SEC column, e.g., to test a pharmaceutical preparation at the point of fill, without complicated extractions or other manipulations (e.g., solvent or solid phase extractions that could affect sample recovery) is one of the advantages of the present invention.

The mobile phase may be an aqueous buffer having a pH between about 2.0 and about 8.0, preferably between about 5.0 and about 7.5, and comprising sufficient salt to prevent the protein in the sample from sticking to the column or SEC medium (e.g., about 50 mM to about 300 mM, preferably about 100 mM to about 200 mM). Appropriate buffers and salts are those listed above for sample preparation. One example of a suitable mobile phase is 140 mM NaCl, 10 mM phosphate, pH 6.45.

The agent that forms a detectable inclusion complex with a cyclodextrin or a cyclodextrin derivative may be brought into contact with any cyclodextrin or cyclodextrin derivative present in a sample before, during, or after the sample is separated by SEC. For example, the agent may be added to a sample before it is loaded on the column, the agent may be present in the mobile phase, the agent may be added to eluate fractions collected from the column, or any combination of the above. In a preferred embodiment the agent is present in the mobile phase.

The agent is selected depending on the cyclodextrin or cyclodextrin derivative to be detected as different cyclodextrins have different binding specificities. Suitable agents are known in the art and may also be determined empirically for each cyclodextrin or cyclodextrin derivative. The agent may have an inherent detectable signal (e.g., fluorescence) or may have a detectable label attached (e.g., a fluorophore or radionuclide). In other embodiments, the agent may have no inherent detectable signal but the inclusion complex formed when the agent binds to a cyclodextrin or cyclodextrin derivative produces a detectable signal. One example of a suitable fluorescent compound for the detection of MBCD is 1-naphthol. Other examples of suitable fluorescent compounds include phenolphthalein and 8-anilinonaphthalene-1-sulfonic acid. If the agent is water soluble it may be added directly to the mobile phase. If the agent is not water soluble it may be dissolved in an organic solvent, including, but not limited to, methanol, ethanol, chloroform, or acetone, and added to the mobile phase such that the percent of organic solvent is low (e.g., less than 10%, preferably less than 9%, 8%, 7%, 6%, 5%, 4%, 3%, 2%, or 1%). The concentration of agent in the mobile phase is sufficient for a signal to be detected. For example, 1-naphthol or other fluorescent compounds may be present in the mobile phase at a concentration of about $1 \times 10^{-8}$ to about $1 \times 10^{-2}$ M, preferably about $1 \times 10^{-5}$ to about $1 \times 10^{-3}$ M, preferably about $1 \times 10^{-4}$ M.

The SEC separation may be performed by methods well known in the art, using suitable column preparation, sample loading, flow rate, fraction collection, and signal detection techniques. See, for example, Deutscher, *Meth. Enzymol.: Guide to Protein Purification*, Vol. 182, Academic Press, Inc., San Diego (1990), Chapter 38; Balch et al., *Meth. Enzymol.*, Vol. 257, Academic Press, Inc., San Diego (1995), Chapter 8); Scopes, Protein Purification: Principles and Practice, Springer-Verlag (1994); Sambrook et al., in Molecular Cloning: A Laboratory Manual; Ausubel et al., Current Protocols in Molecular Biology, each incorporated by reference. In a preferred embodiment the separation is performed by HPLC. The signal detector may be any detector useful for the measurement of the agent, e.g., a fluorescence detector, an ultraviolet detector, or a radiation detector, and may be used in line with the column or separately. When a fluorophore is used as the agent, the fluorescent detector may be set at suitable excitation and emission wavelengths as is known in the art, e.g., 290 nm and 360 nm, respectively, for 1-naphthol. When the cyclodextrin or cyclodextrin derivative is to be quantitated, the size of the detected signal may be measured and compared to a standard curve prepared from samples spiked with increasing amounts of the agent in order to measure the amount of cyclodextrin or cyclodextrin derivative present in the sample.

Using the methods of the invention, the limit of detection of a cyclodextrin or a cyclodextrin derivative may be less than 100 µg/mL, preferably less than 50 µg/mL, 20 µg/mL, 10 µg/mL, 5 µg/mL, 2 µg/mL, or 1 µg/mL.

Proteins, particularly therapeutic proteins, may be purified from cell cultures and prepared as pharmaceutical preparations. Cells may be cultured in the presence of a cyclodextrin or a cyclodextrin derivative, particularly if the cells are dependent on a hydrophobic compound for growth, such as cholesterol auxotrophic cells (e.g., cholesterol auxotrophic derivatives of CHO, COS, or NSO cells). In one aspect of the invention, pharmaceutical preparations may be evaluated for the presence of a cyclodextrin or cyclodextrin derivative.

In the methods of the invention, any cell that is known in the art for protein expression may be used. Examples include NSO cells, monkey COS cells, Chinese Hamster Ovary (CHO) cells, human kidney 293 cells, human epidermal A431 cells, human Colo205 cells, 3T3 cells, CV-1 cells, HeLa cells, and mouse L cells, BHK, HL-60, U937, HaK or Jurkat cells. Cells may be cultured by any method known in the art. In one embodiment, the cells are cholesterol auxotrophic cells (e.g., NSO cells or cells derived therefrom). In another embodiment, the cells are cultured in the presence of MBCD. The cultured cells may naturally express the protein to be purified or be genetically engineered to express the protein. Methods for genetically engineering cells to express a protein of interest are well known in the art. See, for example, Sambrook et al., in Molecular Cloning: A Laboratory Manual; Ausubel et al., Current Protocols in Molecular Biology, each incorporated by reference. The cells are cultured in the presence of the cyclodextrin or cyclodextrin derivative. The protein is then purified from the cultured cells or from the culture medium using techniques well known in the art, e.g., ion exchange chromatography, affinity chromatography, size exclusion chromatography, differential solubility, ultrafiltration, etc. The protein may be purified to at least 90% homogeneity, preferably at least 95%, 96%, 97%, 98%, or 99% homogeneity. The purified protein is then combined with a pharmaceutically acceptable carrier to produce a pharmaceutical preparation.

Pharmaceutically acceptable carriers comprise excipients and additives which facilitate processing of the protein into preparations that can be used pharmaceutically. Examples of excipients include, but are not limited to, water, saline, phosphate buffered saline, dextrose, glycerol, ethanol, and the like. Additives that are well known in the art include, e.g., surfactants (e.g., TWEEN, such as TWEEN-80), detackifiers, anti-foaming agents, buffering agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents, thickening agents, fillers, binders, lubricants, viscomodulators, tonicifiers, flavorants, colorants, odorants, opacifiers, suspending agents, and plasticizers. Preferably, the preparations are suitable solutions for administration by injection or orally and contain about 0.01 to about 99 percent, preferably about 0.25 to about 75 percent of the protein together with the excipient.

The presence of a cyclodextrin or cyclodextrin derivative may be determined at any stage in the purification. In one embodiment, the presence of a cyclodextrin or cyclodextrin derivative is determined in the final pharmaceutical preparation. The method may further comprise making a record (e.g., a print or computer readable record, e.g., a label) of the level of cyclodextrin or cyclodextrin derivative in a sample, e.g., in a finally purified pharmaceutical preparation.

The following examples are illustrative, but not limiting, of the method and compositions of the present invention. Other suitable modifications and adaptations of the variety of conditions and parameters normally encountered in chromatography and pharmaceutical preparation and evaluation and which are obvious to those skilled in the art are within the spirit and scope of the invention.

Example 1

Natilizumab was recombinantly expressed in cholesterol auxotrophic cells cultured in the presence of about 720 mg/L MBCD. The antibody was purified in three routine chromatographic steps. A method for determining the amount of MBCD present after each of the purification steps and in the final antibody preparation (suitable for pharmaceutical use) was developed.

Samples were separated by HPLC on an SEC column (TSK gel G2000SW$_{XL}$, 7.8 mm×30 cm). The mobile phase contained 140 mM NaCl, 10 mM phosphate, pH 6.45/2% (v/v) methanol and $10^{-4}$ M 1-naphthol. Sample sizes were 50 µL (Waters fluorescence detector) or 100 µL (Rainin fluorescence detector). The flow rate was 1 mL/minute under isocratic conditions. The MBCD/1-naphthol inclusion complex was detected using a fluorescence detector at 290 and 360 nm for excitation and emission, respectively.

Limit of detection assays were performed using serial dilution of a MBCD standard (1.0 mg/mL MBCD in water) in an aqueous buffer at pH 6.1. Using this technique the limit of detection was determined to be 1.3 µg/mL. Similar assays were performed to determine the limit of detection in samples of eluate from each of the three chromatographic columns and the final purified antibody preparation. The limit of detection in the samples was very low, ranging from 1.3 µg/mL to 5.2 µg/mL, with an average of 3.0 µg/mL. Representative chromatograms are shown in FIG. 1.

Figure 2:
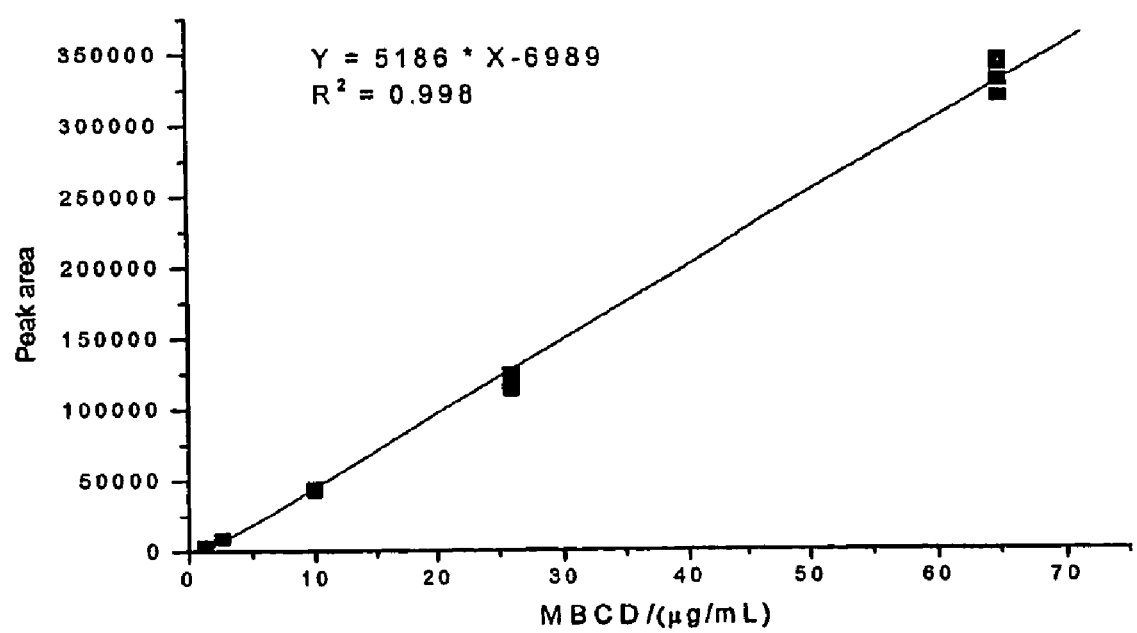
FIG. 2 shows the linearity curve for the MBCD standards.

In order to assess the linearity of the assay, five standards containing 1.3, 2.6, 10, 26, and 65 µg/mL MBCD were injected onto the HPLC column in a volume of 50 µL. The linear least square regression is shown in FIG. 2. The results indicate that the assay has high linearity, with a correlation coefficient of 0.998.

Figure 3:
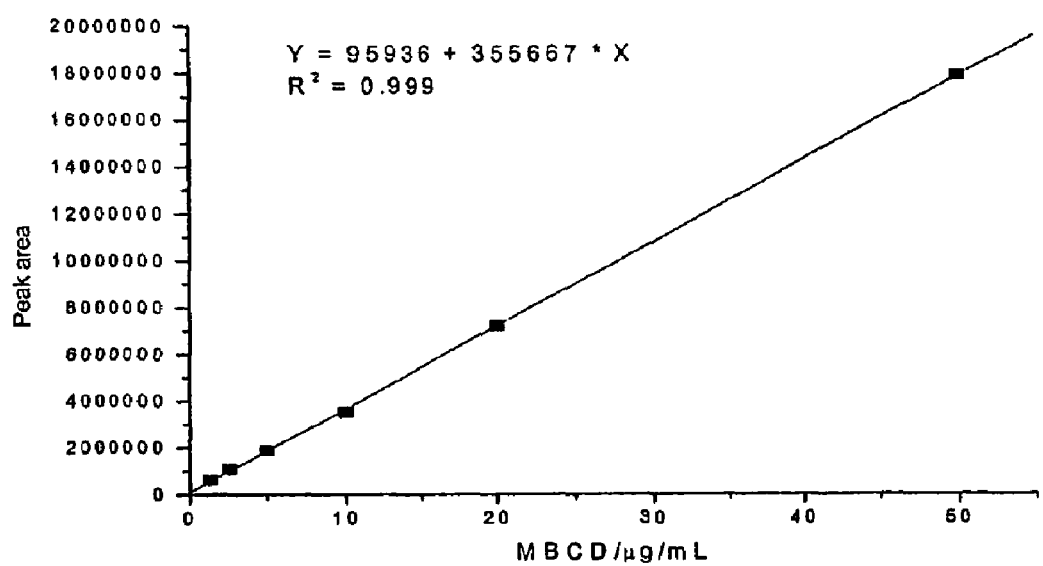
FIG. 3 shows the linearity curve for a pharmaceutical preparation of natilizumab spiked with MBCD.

The linearity was also investigated using samples of the final antibody preparation spiked with 1.3, 2.6, 5.0, 10.0, 20.0, and 50.0 µg/mL MBCD. The results (FIG. 3) show that the assay has high linearity, with a correlation coefficient of 0.999.

The recovery of MBCD in the final antibody preparation was calculated by comparing the peak areas to those of the corresponding MBCD standard. As summarized in Table 1, the recoveries were between 97% and 117% for the MBCD concentrations tested.

TABLE 1

| Concentration (µg/mL) | MBCD Observed (µg/mL) (Average, n = 2) | Recovery (%) |
| --- | --- | --- |
| 1.3 | 1.4 | 112 |
| 2.6 | 3.0 | 117 |
| 5.0 | 4.9 | 98 |
| 10.0 | 9.7 | 97 |
| 20.0 | 21 | 104 |
| 50.0 | 52 | 103 |

The relative standard deviation for repeatability (intra-assay precision) was determined using five standards containing 1.3, 2.6, 10, 26, and 65 µg/mL MBCD. The results are shown in Table 2 and indicate that the assay has a relative standard deviation of less than 5.0%.

TABLE 2

| MBCD (µg/mL) | Observed Values (µg/mL) (n = 5) | Standard Deviation (n = 5) | Percent RSD (n = 5) |
| --- | --- | --- | --- |
| 1.3 | 2.1 | 0.1 | 4.7 |
| 2.6 | 3.1 | 0.1 | 3.2 |
| 10 | 9.6 | 0.2 | 2.1 |
| 26 | 24.6 | 1.1 | 4.4 |
| 65 | 65.6 | 2.0 | 3.1 |

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method for testing for the presence of a cyclodextrin or cyclodextrin derivative in a solution comprising a protein, the method comprising loading a sample of the solution on a size exclusion chromatography (SEC) column, wherein said sample does not undergo a step of extraction prior to being loaded on said column, separating any cyclodextrin or cyclodextrin derivative that may be present from said protein by size exclusion chromatography (SEC), contacting said cyclodextrin or cyclodextrin derivative with an agent that forms a detectable inclusion complex with a separated cyclodextrin or cyclodextrin derivative, and measuring for the presence of a signal from said inclusion complex.

2. The method of claim 1, wherein said cyclodextrin or cyclodextrin derivative is methyl-β-cyclodextrin.

3. The method of claim 1, wherein said protein is a therapeutic protein.

4. The method of claim 1, wherein said protein is a recombinant protein.

5. The method of claim 1, wherein said protein is an antibody.

6. The method of claim 1, wherein said solution comprises less than 20 μg/mL of a cyclodextrin or a cyclodextrin derivative.

7. The method of claim 1, wherein said agent is a fluorescent compound.

8. The method of claim 7, wherein said agent is 1-naphthol.

9. The method of claim 1, wherein said method has a cyclodextrin or a cyclodextrin derivative limit of detection of less than 10 μg/mL.

10. The method of claim 9, wherein said method has a cyclodextrin or a cyclodextrin derivative limit of detection of less than 2 μg/mL.

11. The method of claim 1, wherein said column has a separation range of about 5-20 kDa to about 75-300 kDa.

12. The method of claim 1, wherein said column has a particle size of about 2 to about 6 microns.

13. The method of claim 12, wherein said column has a particle size of about 4 microns.

14. The method of claim 1, wherein said agent is present in the mobile phase during the separating step.

15. The method of claim 1, wherein said separation uses a mobile phase comprising a salt at a concentration of about 50 mM to about 300 mM.

16. The method of claim 1, wherein said sample and said mobile phase have a pH of about 2.0 to about 8.0.

17. The method of claim 16, wherein said sample and said mobile phase have a pH of about 5.0 to about 7.5.

18. The method of claim 1, wherein said protein is at least 90% pure.

19. The method of claim 18, wherein said protein is at least 95% pure.

20. The method of claim 19, wherein said protein is at least 98% pure.

21. A method for determining the quantity of a cyclodextrin or cyclodextrin derivative that may be present in a solution comprising a protein, the method comprising loading a sample of the solution on a size exclusion chromatography (SEC) column, wherein said sample does not undergo a step of extraction prior to being loaded on said column, separating any cyclodextrin or cyclodextrin derivative from said protein by SEC, contacting said cyclodextrin or cyclodextrin derivative with an agent that forms a detectable inclusion complex with a separated cyclodextrin or cyclodextrin derivative, measuring for the presence of a signal from said inclusion complex, and determining the size of said signal, wherein the size of the signal is indicative of the quantity of the cyclodextrin or cyclodextrin derivative in the solution.

22. The method of claim 12, wherein said cyclodextrin or cyclodextrin derivative is methyl-β-cyclodextrin.

23. The method of claim 21, wherein said protein is a therapeutic protein.

24. The method of claim 21, wherein said protein is a recombinant protein.

25. The method of claim 21, wherein said protein is an antibody.

26. The method of claim 21, wherein said solution comprises less than 20 μg/mL of a cyclodextrin or a cyclodextrin derivative.

27. The method of claim 21, wherein said agent is a fluorescent compound.

28. The method of claim 27, wherein said agent is 1-naphthol.

29. The method of claim 21, wherein said method has a cyclodextrin or a cyclodextrin derivative limit of detection of less than 10 μg/mL.

30. The method of claim 29, wherein said method has a cyclodextrin or a cyclodextrin derivative limit of detection of less than 2 μg/mL.

31. The method of claim 21, wherein said column has a separation range of about 5-20 kDa to about 75-300 kDa.

32. The method of claim 21, wherein said column has a particle size of about 2 to about 6 microns.

33. The method of claim 32, wherein said column has a particle size of about 4 microns.

34. The method of claim 21, wherein said agent is present in the mobile phase during the separating step.

35. The method of claim 21, wherein said separation uses a mobile phase comprising a salt at a concentration of about 50 mM to about 300 mM.

36. The method of claim 21, wherein said sample and said mobile phase have a pH of about 2.0 to about 8.0.

37. The method of claim 36, wherein said sample and said mobile phase have a pH of about 5.0 to about 7.5.

38. The method of claim 21, wherein said protein is at least 90% pure.

39. The method of claim 38, wherein said protein is at least 95% pure.

40. The method of claim 39, wherein said protein is at least 98% pure.

41. A method of evaluating a pharmaceutical preparation, the method comprising: (a) providing a pharmaceutical preparation comprising a therapeutic protein and a pharmaceutically acceptable carrier; (b) loading a sample of said pharmaceutical preparation on a size exclusion chromatography (SEC) column, wherein the sample does not undergo a step of extraction prior to being loaded on said column, (c) separating said pharmaceutical preparation by SEC; (d) contacting any cyclodextrin or cyclodextrin derivative that may be present in the pharmaceutical preparation with an agent that forms a detectable inclusion complex with a separated cyclodextrin or cyclodextrin derivative; and (e) detecting a signal from said inclusion complex, wherein the size of the signal is indicative of the quantity of the cyclodextrin or cyclodextrin derivative in the preparation.

42. The method of claim 41, wherein said cyclodextrin or cyclodextrin derivative is methyl-β-cyclodextrin.

43. The method of claim 41, wherein said protein is a recombinant protein.

44. The method of claim 41, wherein said protein is an antibody.

45. The method of claim 41, wherein said protein is a monoclonal antibody.

46. The method of claim 41, wherein said solution comprises less than 20 μg/mL of a cyclodextrin or a cyclodextrin derivative.

47. The method of claim 41, wherein said agent is a fluorescent compound.

48. The method of claim 47, wherein said agent is 1-naphthol.

49. The method of claim 41, wherein said method has a cyclodextrin or a cyclodextrin derivative limit of detection of less than 10 μg/mL.

50. The method of claim 49, wherein said method has a cyclodextrin or a cyclodextrin derivative limit of detection of less than 2 μg/mL.

51. The method of claim 41, wherein said column has a separation range of about 5-20 kDa to about 75-300 kDa.

52. The method of claim 41, wherein said column has a particle size of about 2 to about 6 microns.

53. The method of claim 41, wherein said column has a particle size of about 4 microns.

54. The method of claim 41, wherein said agent is present in the mobile phase during the separating step.

55. The method of claim 41, wherein said separation uses a mobile phase comprising a salt at a concentration of about 50 mM to about 300 mM.

56. The method of claim 41, wherein said sample and said mobile phase have a pH of about 2.0 to about 8.0.

57. The method of claim 56, wherein said sample and said mobile phase have a pH of about 5.0 to about 7.5.

58. The method of claim 41, wherein said protein is at least 90% pure.

59. The method of claim 58, wherein said protein is at least 95% pure.

60. The method of claim 59, wherein said protein is at least 98% pure, on.

* * * * *